(12) United States Patent
Duque

(10) Patent No.: US 8,146,179 B1
(45) Date of Patent: Apr. 3, 2012

(54) URINATION CANAL FOR FEMALES

(76) Inventor: Felix D. Duque, Homestead, FL (US)

(*) Notice: Subject to any disclaimer, the term of this patent is extended or adjusted under 35 U.S.C. 154(b) by 488 days.

(21) Appl. No.: 12/487,810

(22) Filed: Jun. 19, 2009

(51) Int. Cl.
*A47K 11/00* (2006.01)
(52) U.S. Cl. ............ 4/144.4; 4/144.1; 4/144.2; 4/144.3
(58) Field of Classification Search ......... 4/144.1–144.4
See application file for complete search history.

(56) References Cited

U.S. PATENT DOCUMENTS

| 2,878,486 | A | * | 3/1959 | Bartlett et al. | 4/144.4 |
| 4,023,216 | A | * | 5/1977 | Li | 4/144.3 |
| 5,742,948 | A | * | 4/1998 | Cicio | 4/144.3 |
| 6,202,224 | B1 | * | 3/2001 | Freeman | 4/144.2 |

* cited by examiner

*Primary Examiner* — Tuan Nguyen
(74) *Attorney, Agent, or Firm* — Albert Bordas, P.A.

(57) ABSTRACT

A urination canal for females, consisting of a funnel assembly comprising first and second walls. The first and second walls are joined at a top ridge, a bottom ridge, and a rear ridge. A pocket assembly is mounted onto the first wall. The pocket assembly is defined by a third wall having first, second, third and fourth ends. The first end has a tab extending therefrom, and the pocket assembly houses a moist towelette.

20 Claims, 3 Drawing Sheets

URINATION CANAL FOR FEMALES

BACKGROUND OF THE INVENTION

1. Field of the Invention

The present invention relates to an apparatus to aid females while urinating, and more particularly, to urination canals.

2. Description of the Related Art

Often time women need to urinate in public restroom facilities. Unfortunately, some public restroom facilities are not clean and hygienic, and furthermore do not have toilet paper or napkins. Not wanting to sit on a toilet seat that is not clean and hygienic, some women prefer to urinate while standing or while in a semi-squatting position, if they are able to. Applicant is not aware of any urination canals ergonomically designed to be positioned at a women's crotch area to receive and direct a stream of urine that also comprises a pocket assembly to house a moist towelette.

SUMMARY OF THE INVENTION

The instant invention is a urination canal ergonomically designed to be positioned at a women's crotch area to receive and direct a stream of urine that also comprises a pocket assembly to house a moist towelette.

More specifically, the instant invention is a urination canal for females, consisting of a funnel assembly comprising first and second walls. The first and second walls are joined at a top ridge, a bottom ridge, and a rear ridge. A pocket assembly is mounted onto the first wall. The pocket assembly is defined by a third wall having first, second, third and fourth ends. The first end has a tab extending therefrom, and the pocket assembly houses a moist towelette.

The first wall comprises first and second edges, and the second wall comprises third and fourth edges. The top ridge is shorter in length than the bottom ridge. The pocket assembly is smaller in surface area than the first wall, and the first and second walls are identical in shape and size.

A first opening defined by the first and third edges is greater in size than a second opening defined by the second and fourth edges. A first predetermined force is placed upon the top ridge and the bottom ridge to cause the first and third edges to separate a first predetermined distance. The first predetermined force causes the second and fourth edges to separate a second predetermined distance. The first predetermined force is applied upon the top ridge and the bottom ridge at a third predetermined distance from the second and fourth edges without reaching the first and third edges.

A first angle created by the bottom and rear edges is greater than a second angle created by the bottom ridge and the second and fourth edges. The first angle is greater than a third angle created by the rear ridge and the first and third edges. The first angle is also greater than a fourth angle created by the top ridge and the first and third edges. The first and third edges are concave in shape. The funnel assembly is made of an impermeable material, and the pocket assembly is hermetically sealed. The third wall is partially removable from the first wall.

It is therefore one of the main objects of the present invention to provide an ergonomically designed urination canal to be positioned at a women's crotch area to receive and direct a stream of urine that also comprises a pocket assembly to house a moist towelette.

It is another object of this invention to provide an ergonomically designed urination canal for females that is disposable.

It is another object of this invention to provide an ergonomically designed urination canal for females that is volumetrically efficient for carrying, transporting, and storage.

It is still another object of this invention to provide an ergonomically designed urination canal for females, which sanitarily protects females while urinating in a standing position and away from a toilet.

It is still another object of this invention to provide an ergonomically designed urination canal for females that may be used by simply unzipping an outer garment or pulling a skirt to a side.

It is still another object of this invention to provide an ergonomically designed urination canal for females, which allows the use of its handy wipes rather than toilet paper.

It is yet another object of this invention to provide an ergonomically designed urination canal for females that is ready and easy to use in places such as public restrooms, airplanes, buses, trains, nightclubs, beaches, while camping, and in other instances when away from home.

It is yet another object of this invention to provide such a device that is inexpensive to manufacture while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
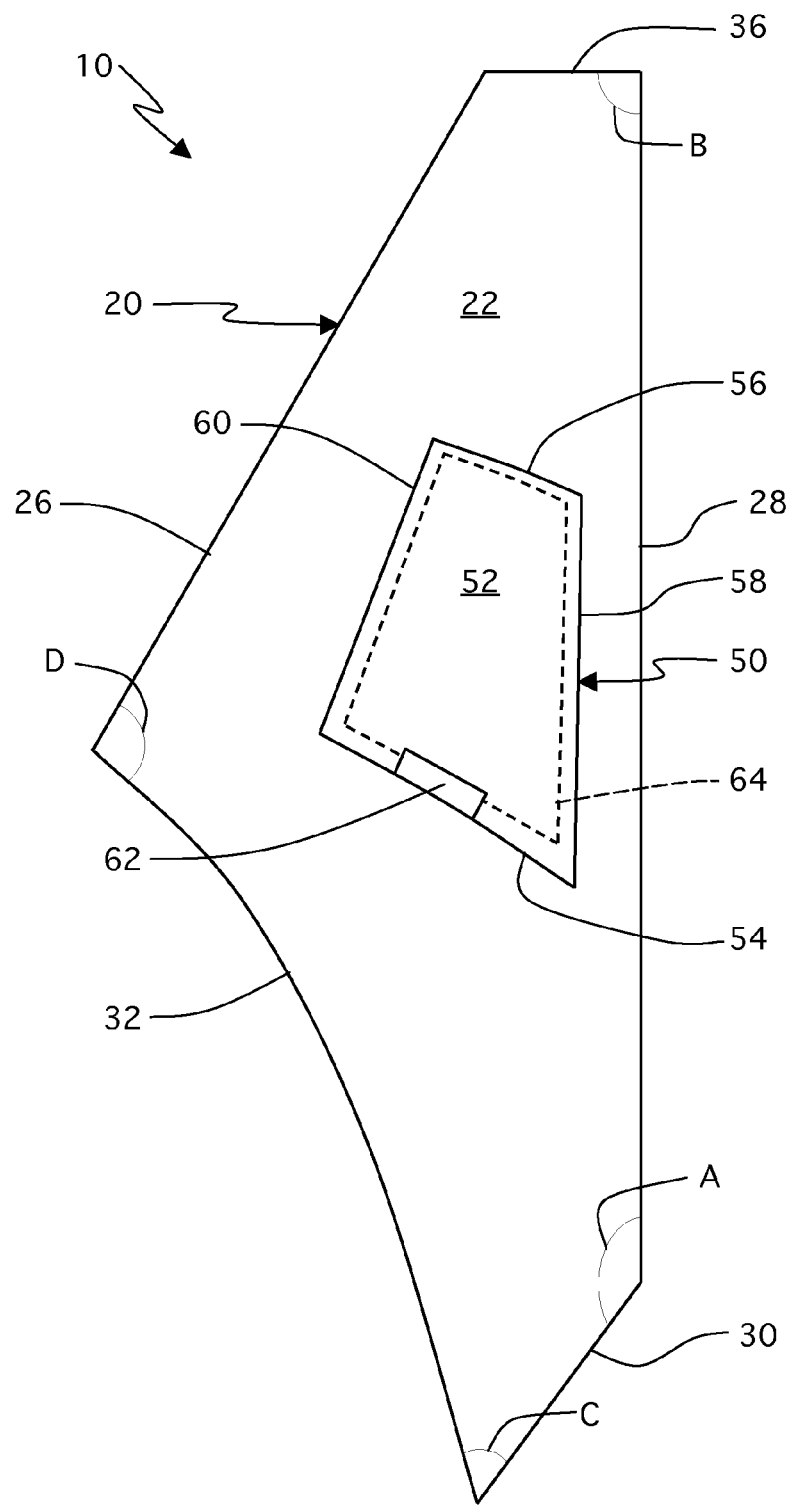
FIG. 1 is a front view of the instant invention.

Referring now to the drawings, the present invention is generally referred to with numeral 10. It can be observed that it basically includes funnel assembly 20 and pocket assembly 50.

Figure 2:
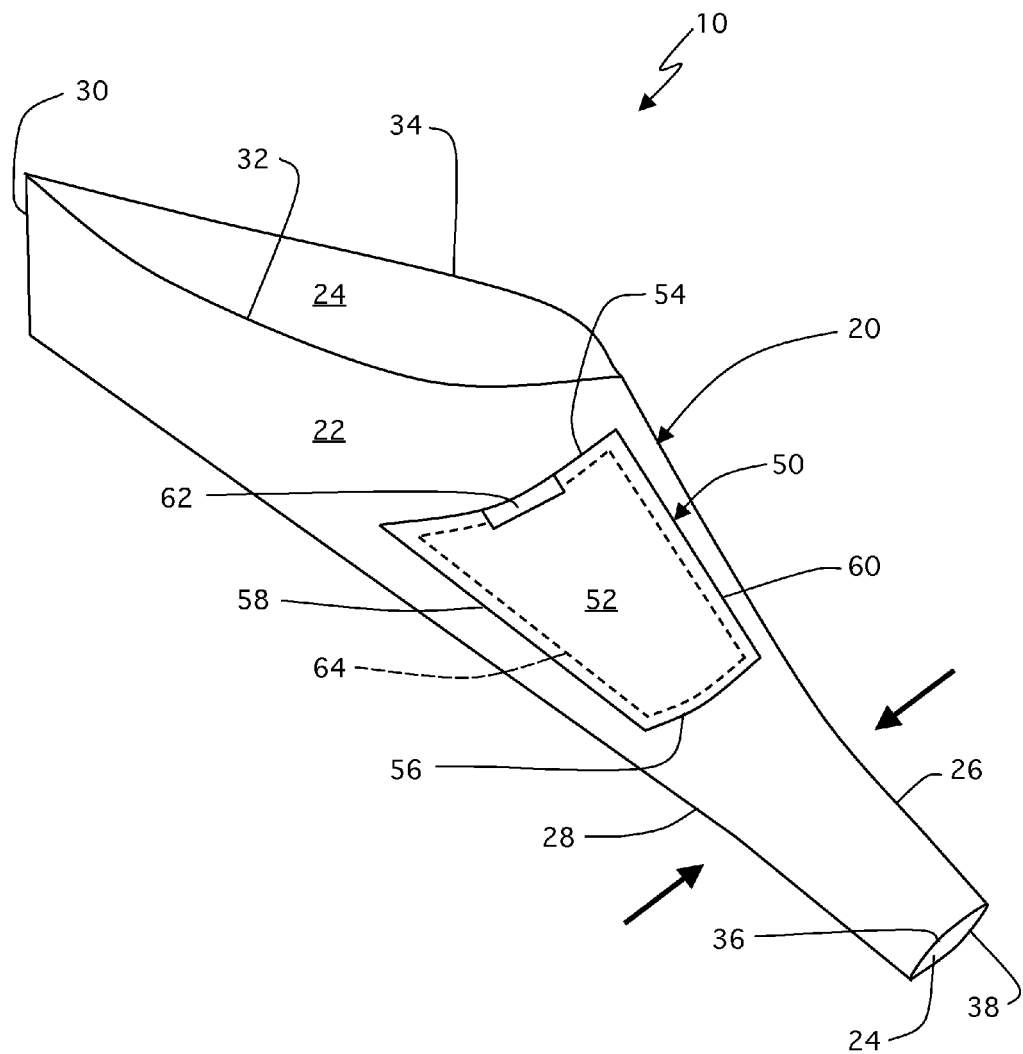
FIG. 2 is an isometric view of the instant invention.

As seen in FIGS. 1 and 2, funnel assembly 20 comprises walls 22 and 24, which are identical in shape and size, and are joined to each other at top ridge 26, bottom ridge 28, and rear ridge 30. Top ridge 26 is shorter in length than bottom ridge 28. Wall 22 comprises edges 32 and 36. Wall 24 comprises edges edge 34 and 38. Edges 32 and 34 are concave in shape and they define a first opening. Edges 36 and 38 define a second opening. The first opening defined by edges 32 and 34 is greater in size than the second opening defined by edges 36 and 38.

First angle A is defined by bottom ridge 28 and rear ridge 30. In the preferred embodiment, first angle A is in between 145 and 155 degrees. Second angle B is defined by bottom ridge 28 and edges 36 and 38. In the preferred embodiment, second angle B is in between 85 and 95 degrees. Third angle C is defined by rear ridge 30 and edges 32 and 34. In the preferred embodiment, third angle C is in between 25 and 35 degrees. Fourth angle D is defined by top ridge 26 and edges 32 and 34. In the preferred embodiment, fourth angle D is in between 95 and 105 degrees. First angle A is greater than second angle B. First angle A is also greater than third angle C and fourth angle D.

Pocket assembly 50 is mounted onto wall 22. Pocket assembly 50 is hermetically sealed, and houses moist towelette 64. Pocket assembly 50 is smaller in surface area than wall 22. Pocket assembly 50 is defined by wall 52. Wall 52 comprises rear end 54, front end 56, bottom end 58, and top end 60. Rear end 54 has tab 62 extending therefrom. Wall 52 is partially removable from wall 22. In the preferred embodiment, funnel assembly 20 is made of an impermeable material, such as polypropylene.

As best seen in FIG. 2, when a predetermined force is applied upon top ridge 26 and bottom ridge 28, it causes edges 32 and 34 to separate from each other a first predetermined distance, and edges 36 and 38 to separate from each other a second predetermined distance. This predetermined force is applied upon top ridge 26 and bottom ridge 28 at a third predetermined distance from edges 36 and 38 without reaching edges 32 and 34.

Figure 3:
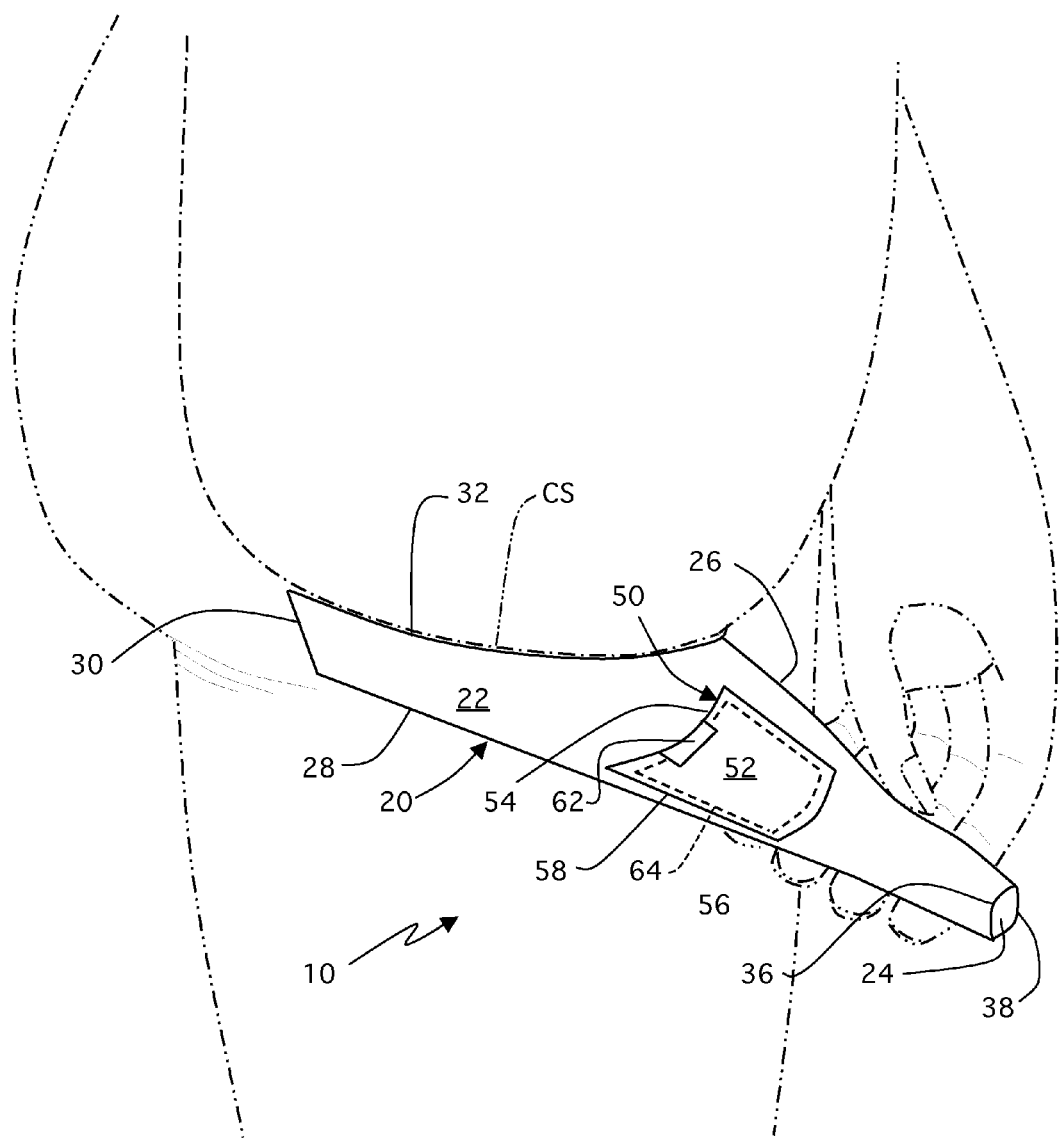
FIG. 3 is an isometric view of the instant invention positioned at a women's crotch section to receive and direct a stream of urine.

In use as seen in FIG. 3, instant invention 10 is positioned at a user's crotch section CS while in a standing position, whereby rear ridge 30 is in the direction of the user's anus. The user then applies the predetermined force to top ridge 26 and bottom ridge 28, causing edges 32 and 34 to separate from each other the first predetermined distance, and edges 36 and 38 to separate from each other the second predetermined distance. The user then places edges 32 and 34 with an upward force, up and around, her urethra at crotch section CS.

The human female urethra is approximately 1½-2 inches (3-5 cm) long and opens between the clitoris and the vaginal opening, extending from the internal to the external urethral orifice. It is placed behind the symphysis pubis, embedded in the anterior wall of the vagina, and its direction is obliquely downward and forward; it is slightly curved with its concavity directed forward. Its lining is composed of stratified squamous epithelium, which becomes transitional near the bladder. The urethra consists of three coats: muscular, erectile, and mucous, the muscular layer being a continuation of that of the bladder. Between the superior and inferior fascia of the urogenital diaphragm, the female urethra is surrounded by the Sphincter urethae. Somatic innervation of the external urethral sphincter is supplied by the pudendal nerve. The urogenital sinus may be divided into three component parts. The first of these is the cranial portion, which is continuous with the allantois and forms the bladder proper. The pelvic part of the sinus forms the prostatic urethra and epithelium as well as the membranous urethra and part of the vagina.

Once in position as illustrated in FIG. 3, the user urinates. Funnel assembly 20 receives and directs the urine stream so that it exists from the second opening defined by edges 36 and 38. The urine stream may flow into a toilet, urinal, or any suitable container for this purpose.

Once urination is complete, the user pulls tab 62 to partially remove wall 52 from wall 22, and removes moist towelette 64 to clean herself. Instant invention 10 is then discarded.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A urination canal for females, consisting of:
    A) a funnel assembly comprising first and second walls, said first and second walls joined at a top ridge, a bottom ridge, and a rear ridge; and
    B) a pocket assembly mounted onto said first wall, said pocket assembly defined by a third wall having first, second, third and fourth ends, said first end having a tab extending therefrom, said pocket assembly housing a moist towelette.

2. The urination canal for females set forth in claim 1, further characterized in that said first wall comprises first and second edges.

3. The urination canal for females set forth in claim 2, further characterized in that said second wall comprises third and fourth edges.

4. The urination canal for females set forth in claim 3, further characterized in that a first opening defined by said first and third edges is greater in size than a second opening defined by said second and fourth edges.

5. The urination canal for females set forth in claim 3, further characterized in that a first predetermined force is placed upon said top ridge and said bottom ridge to cause said first and third edges to separate a first predetermined distance.

6. The urination canal for females set forth in claim 5, further characterized in that said first predetermined force causes said second and fourth edges to separate a second predetermined distance.

7. The urination canal for females set forth in claim 6, further characterized in that said first predetermined force is applied upon said top ridge and said bottom ridge at a third predetermined distance from said second and fourth edges without reaching said first and third edges.

8. The urination canal for females set forth in claim 3, further characterized in that a first angle created by said bottom and rear edges is greater than a second angle created by said bottom ridge and said second and fourth edges.

9. The urination canal for females set forth in claim 8, further characterized in that said first angle is greater than a third angle created by said rear ridge and said first and third edges.

10. The urination canal for females set forth in claim 9, further characterized in that said first angle is greater than a fourth angle created by said top ridge and said first and third edges.

11. The urination canal for females set forth in claim 3, further characterized in that said first and third edges are concave in shape.

12. The urination canal for females set forth in claim 1, further characterized in that said top ridge is shorter in length than said bottom ridge.

13. The urination canal for females set forth in claim 1, further characterized in that said pocket assembly is smaller in surface area than said first wall.

14. The urination canal for females set forth in claim 1, further characterized in that said first and second walls are identical in shape and size.

15. The urination canal for females set forth in claim 1, further characterized in that said funnel assembly is made of an impermeable material.

16. The urination canal for females set forth in claim 1, further characterized in that said pocket assembly is hermetically sealed.

17. The urination canal for females set forth in claim 1, further characterized in that said third wall is partially removable from said first wall.

18. A urination canal for females, consisting of:
    A) a funnel assembly comprising first and second walls, said first and second walls joined at a top ridge, a bottom ridge, and a rear ridge, said first wall comprises first and second edges, said second wall comprises third and fourth edges, said top ridge is shorter in length than said bottom ridge, said first and second walls are identical in shape and size; and B) a pocket assembly mounted onto said first wall, said pocket assembly defined by a third wall having first, second, third and fourth ends, said first end having a tab extending therefrom, said pocket assembly housing a moist towelette, said pocket assembly is smaller in surface area than said first wall.

19. The urination canal for females set forth in claim 18, further characterized in that a first opening defined by said first and third edges is greater in size than a second opening defined by said second and fourth edges, further characterized in that a first predetermined force is placed upon said top ridge and said bottom ridge to cause said first and third edges to separate a first predetermined distance, said first predetermined force causes said second and fourth edges to separate a second predetermined distance, and said first predetermined force is applied upon said top ridge and said bottom ridge at a third predetermined distance from said second and fourth edges without reaching said first and third edges.

20. The urination canal for females set forth in claim 18, further characterized in that a first angle created by said bottom and rear edges is greater than a second angle created by said bottom ridge and said second and fourth edges, said first angle is greater than a third angle created by said rear ridge and said first and third edges, said first angle is also greater than a fourth angle created by said top ridge and said first and third edges, and said first and third edges are concave in shape.

\* \* \* \* \*